United States Patent [19]

Doherty

[11] Patent Number: 5,767,942
[45] Date of Patent: Jun. 16, 1998

[54] HAND-HELD SLIT LAMP APPARATUS AND ASSOCIATED METHODS

[76] Inventor: Victor J. Doherty, 32 Sterling Rd., Wellesley, Mass. 02181

[21] Appl. No.: 822,066

[22] Filed: Mar. 24, 1997

Related U.S. Application Data

[62] Division of Ser. No. 545,551, Oct. 19, 1995, Pat. No. 5,638,150.

[51] Int. Cl.⁶ .............................. A61B 3/00; A61B 3/10
[52] U.S. Cl. ................................. 351/218; 351/218
[58] Field of Search ........................... 351/246, 218, 351/205, 200

[56] References Cited

U.S. PATENT DOCUMENTS

| | | |
|---|---|---|
| 3,379,110 | 4/1968 | Blackert et al. |
| 3,403,957 | 10/1968 | Wilkinson ............ 351/38 |
| 3,405,994 | 10/1968 | Altmsn et al. |
| 3,407,019 | 10/1968 | Wikinson |
| 3,460,560 | 8/1969 | Kah, Jr. et al. |
| 3,467,466 | 9/1969 | Binstead et al. |
| 3,533,685 | 10/1970 | Litmann et al. |
| 3,535,027 | 10/1970 | Littmann et al. |
| 3,776,619 | 12/1973 | Heine ............ 351/218 |

*Primary Examiner*—Hung X. Dang
*Attorney, Agent, or Firm*—Curtis A. Vock

[57] ABSTRACT

A hand-held slit lamp instrument has a substantially elongated handle that houses one or more batteries and that connects to a line filament lamp. A front knob is threaded to the handle so that it is rotatable about the elongated axis of the handle. The front knob has an internal hollow section that houses one or more imaging elements to generate a slit image of the line filament out through an aperture in the front knob and away from the instrument. The rotation of the front knob axially displaces the imaging elements relative to the lamp to control the magnification and distance of the slit image. A rear knob also threads to the handle and rotates about the axis to provide an electrical switch. The rotation of the rear knob displaces the rear knob relative to the handle and between a first "ON" position and a second "OFF" position. A retaining ring, e.g., a Smalley ring, is mounted into a groove in the handle and between the handle and a groove in the rear knob, to provide a mechanical and tamper-proof stop between the first and second positions. A window in the front knob provides a visual indication of whether the light filament is on.

3 Claims, 9 Drawing Sheets

HAND-HELD SLIT LAMP APPARATUS AND ASSOCIATED METHODS

This is a division of application Ser. No. 08/545,551 filed on Oct. 19, 1995, now U.S. Pat. No. 5,638,150.

BACKGROUND

Slit lamps are commonly used by opthamologists to examine the human eye. Such lamps typically operate to project a relatively narrow beam of light into a patient's pupil so that the physician can spatially inspect the illuminated regions of the vitreous humour, cornea, anterior chamber, iris, lens and retina. Accordingly, the slit lamps of the prior art are generally constructed into a combination apparatus that includes (i) a series of optical elements to form a slit image of an optical source onto the patient's eye, (ii) a microscope to examine the regions illuminated by the slit image, and (iii) a supporting structure to interface with and immobilize the patient's head.

The complexity and weight of these slit lamps make them generally inappropriate for the bedside examination of adults, and for the examination of infants and other children who tend to resist a structured and still position. In addition, such lamps are quite expensive and can be unaffordable to small clinics.

Hand-held slit lamps are also provided in the prior art. One such slit lamp is described in a 1965 article by Emanuel Krimsky, M.D., entitled "A New Hand Slit Lamp to fit a Penlight Battery Handle." The prior art slit lamp described in this article utilizes a pair of plano-convex lenses to image a straight-filament lamp onto a patient's eye. A standard pen-light battery handle is coupled to the filament and lenses to form an integral and self-powered portable slit lamp unit.

The hand-held slit lamps of the prior art, such as the portable unit described by Dr. Krimsky, have several problems. For example, they are inflexible and thus offer little if any control over the instrument's performance; and they suffer from mechanical short-comings which limit their durability and safety in a clinical environment.

Further, the commercially-available portable slit-lamps are relatively complex, which raises manufacturing and consumer costs. As such, certain rural clinics, and particularly the clinics of under-developed nations, are unable to afford the devices and to benefit by their use.

It is, accordingly, an object of the invention to provide an improved hand-held slit lamp which reduces or eliminates the afore-mentioned problems.

Another object of the invention is to provide a hand-held slit-lamp which is durable and easily controlled by a user of the lamp.

Still another object of the invention is to provide methods for illuminating and controlling a slit image into a patient's eye.

These and other objects will become apparent in the description which follows.

SUMMARY OF THE INVENTION

In one aspect, the invention provides a hand-held slit lamp instrument. The instrument includes a handle that forms an elongated axis between a distal end and a proximal end. The handle also forms a first hollow interior along at least part of the axis so that one or more batteries can be disposed within the first hollow interior. A light source, such as a line filament, is mounted with the handle and connected to the batteries to emit light energy selectively. A first knob is rotatably threaded with the distal end of the handle. The first knob is concentric with the axis and forms a second hollow interior along the axis. The first knob is rotatable, relative to the handle, to control the axial displacement of the first knob relative to the handle. The first knob and the handle substantially enclose the light source; and the first knob has an optical aperture to transmit the light energy out of and away from the instrument. One or more optical elements within the first knob provide a slit image of the light source through the optical aperture and at a selected working distance away from the instrument. A user of the instrument controls the instrument's magnification, and hence the width and height of the slit image, by rotating the first knob about the elongated axis.

In another aspect, the instrument of the invention includes a first O-ring mounted between the first knob and the handle. The first O-ring seals out moisture and other particulates from the first and second interiors.

In yet another aspect, the instrument includes a second knob that is rotatably threaded with the proximal end of the handle. The second knob is concentric with the axis and rotatable, relative to the handle, to control the axial displacement of the second knob between a first position and a second position. An electrical switch is responsive to the axial movement of the second knob to complete a circuit between the batteries and the lamp when the second knob is in the first position. The switch also breaks the circuit when the second knob is in the second position. A second O-ring can be included between the second knob and the handle, to seal out moisture and other particulates from the switch.

The invention preferably includes a window within the first knob. The window is transparent to the energy from the light source, and thus provides an indication as to whether the light source is on within the instrument.

In still another aspect, the first knob and optics can be replaced by a zoom lens that is rotatably threaded with the distal end of the handle. The zoom lens is concentric with the axis and is rotatable, relative to the handle, to control the axial displacement of the zoom lens relative to the handle. The zoom lens has a zoom ring to adjust the magnification of the zoom lens selectively, and has an optical aperture to transmit the light energy out of and away from the instrument. The zoom lens forms a slit image of the light source through the optical aperture and at a selected working distance away from the instrument. In combination, the zoom ring and the zoom lens rotation permit the independent control of the working distance and slit image magnification.

In another aspect, the invention provides a tamper-proof electrical switch. An elongated inner body has a first outer diameter and a relay for connecting the inner body to a power source. The inner body has a first outer groove with a second outer diameter that is less than the first outer diameter. A C-ring mounts with the outer groove and has (i) a first inner diameter that is greater than the second outer diameter and less than the first outer diameter, and (ii) a third outer diameter that is greater than the first outer diameter. The C-ring is flexible to sustain temporary compression of the first inner diameter. An elongated outer body is rotatably threaded with the inner body. The outer body is rotatable relative to the inner body to control the axial displacement of the outer body. The outer body has a second inner diameter that is greater than the first outer diameter and less than the third outer diameter; and an inner groove with an inner diameter that is greater than the third outer diameter. The inner groove and the outer groove are substantially concentric such that the C-ring forms a stop against the inner groove and between a first position and a second position. A connector is responsive to the axial displacement of the outer body, and (i) engages the relay at the first position to complete a circuit with the power source, and (ii) disengages the relay at the second position to break the circuit. Preferably, the C-ring is a Smalley ring.

The invention thus provides several advantages. First, the hand-held slit lamp of the invention is suitable for use with patients of all ages and sizes. It not only produces a high quality and bright beam of selectable size, it can be operated comfortably in one hand. By way of example, the slit lamp of the invention is easily controlled to modify the working distance to the patient and/or the size of the slit image.

The invention is clinically useful, for example, in the inspection and assessment of infant cataracts and glaucoma patients, breaks in the Descamet's membrane, iris detail, and of cataract morphology. It is especially useful in monitoring the anterior chamber depth during the post-operative hypotony phase of a trabeculectomy.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which.

DETAILED DESCRIPTION OF THE DRAWINGS

Figure 1:
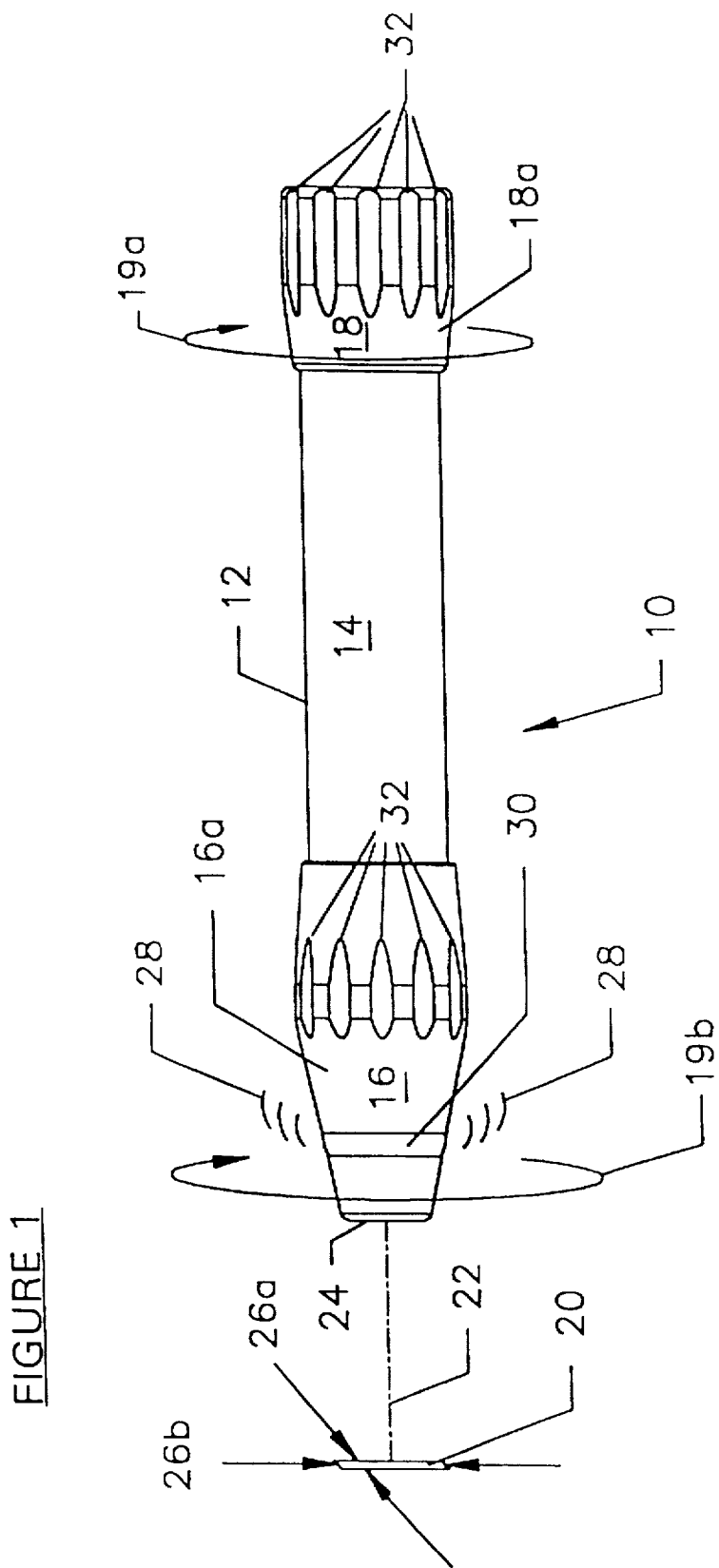
FIG. 1 illustrates one hand-held slit-lamp constructed according to the invention.

FIG. 1 illustrates a hand-held slit-lamp instrument 10 constructed according to the invention. Briefly, FIG. 1 illustrates the overall operation of the slit-lamp relative to the function of the outer body 12, which includes a handle 14, front knob 16 and rear knob 18. A user rotates the rear knob 18, such as illustrated by arrow 19a, to turn on the instrument 10 so that a slit image 20 is formed at a working distance 22 away from the front 24 of knob 16. A user turns the front knob 16, such as illustrated by arrow 19b, to vary the working distance 20 and/or to vary the width 26a and length 26b of the slit image 20. When the instrument 10 is "ON," a light from within the body 12 emits visible radiation 28 through a transparent window 30 so that the user knows that the instrument is "ON." The window 30 is preferably a red color and is ring-shaped around the circumference of the instrument 10 so that the emitted radiation is comfortably viewable from any practical angle.

In the preferred embodiment of the invention, each of the knobs 16, 18 has a series of grips 32 formed integrally within the surfaces 16a, 18a, respectively. The grips 32 provide a firm grip from which the user can grasp and rotate the knobs 16, 18 without difficulty.

The body 12 is preferably formed of anodized aluminum. The knobs 16, 18 engage the handle 14 by way of o-ring seals (not shown in FIG. 1) to prevent dust and moisture from entering into the body 12 and from affecting the several elements therein.

Figure 2:
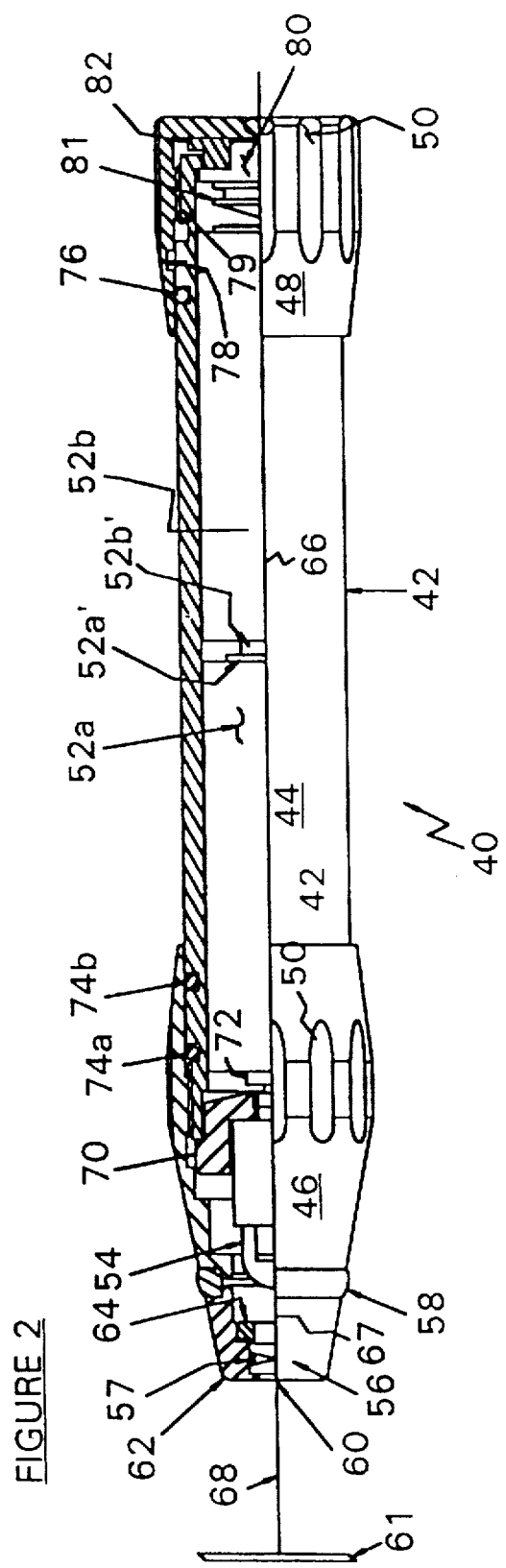
FIG. 2 shows an assembly drawing of a hand-held slit lamp instrument constructed according to the invention.

FIG. 2 shows a schematic assembly drawing, partially cut-away, of a slit-lamp 40 constructed according to the invention. As above, an outer body 42 includes a front knob 46 and rear knob 48, each with associated grips 50, and an electrically conductive handle portion 44. The body 42 houses two AA batteries 52a, 52b, a line filament lamp 54, and a set of optics 56, each of which is described in greater below. A window 58, such as the window 30 of FIG. 1, transmits light energy emitted from the lamp 54 so that a user can detect when the instrument 40 is "ON."

Much of the light energy from the lamp 54 is collected by the optical elements 56, here shown as a plano-convex pair separated by a spacer 57, and transmitted through the front lens surface 60 to form a slit image 61, such as described herein. The elements 56 are mounted within the nose 62 of the instrument 40 by way of a retainer 64; and are thus substantially held in a fixed position within the knob 46.

With the handle 44 positioned at a fixed axial location, the lenses 56 move axially along the elongated axis 66 when the front knob 46 is rotated relative to the handle 44, such as described in connection with FIG. 1. More particularly, the knob 46 is threaded to the handle 44, in a manner which is described in more detail below, so that rotation of the knob 46 changes the distance 67 between the optics 56 and the filament 54. When the distance 67 changes, the magnified size of the slit image 61 changes, as does the working distance 68 between the nose 62 and the image 61.

The line filament 54 abuts a retaining element 70 which holds the filament 54 and which maintains electrical continuity with the filament's electrodes 54a, 54b (shown in FIG. 2A) so as to communicate electrical energy between the filament 54 and the electrically conductive handle 44. Typically, the filament 54 includes a center electrode 54b and a brass casing 54a, which forms the other electrode. The electrodes 54a, 54b, retainer 70 and handle 44 form an integral part of the circuit which energizes the filament 54, such as described in more detail below.

The knob 46 is sealed to the handle 44 by way of two O-rings 74a, 74b, which snugly fit between the knob 46 and handle 44. The O-rings 74a, 74b help prevent moisture from seeping into instrument 40, and further provide a source of friction which enhances the smooth rotation of the knob 46 about the axis 66.

Knob 48 functions as an electrical switch when it is rotated about the axis 66. As above, the knob 48 is threaded to the handle 44, described in more detail below, and sealed by way of O-ring 76 to minimize or reduce the amount of moisture and/or particulates which enter the instrument 40.

A retaining ring 78 forms a hard stop with the knob 48 in two separate locations, representing "ON" and "OFF" positions, such as described-below. When the knob 48 is rotated to the "ON" position, an electrical contact 79 completes an electrical circuit with the spring mount 80—coupled by conductive springs 81 to the battery 52b—so that the batteries 52a, 52b provide electrical power the lamp 54 (note that the batteries 52a, 52b abut one another at juncture 82 so that the negative pole 52a' of battery 52a contacts the position pole 52b' of battery 52b).

The instrument 40 is turned "OFF" when a user rotates the knob 48 about the axis 66 such that the plastic insulator 82 engages the mount 80 to break the circuit between the electrical contact 79 and the mount 80. This, in turn, decouples the batteries from the filament circuit, and turns off the filament 54.

Figure 2A:
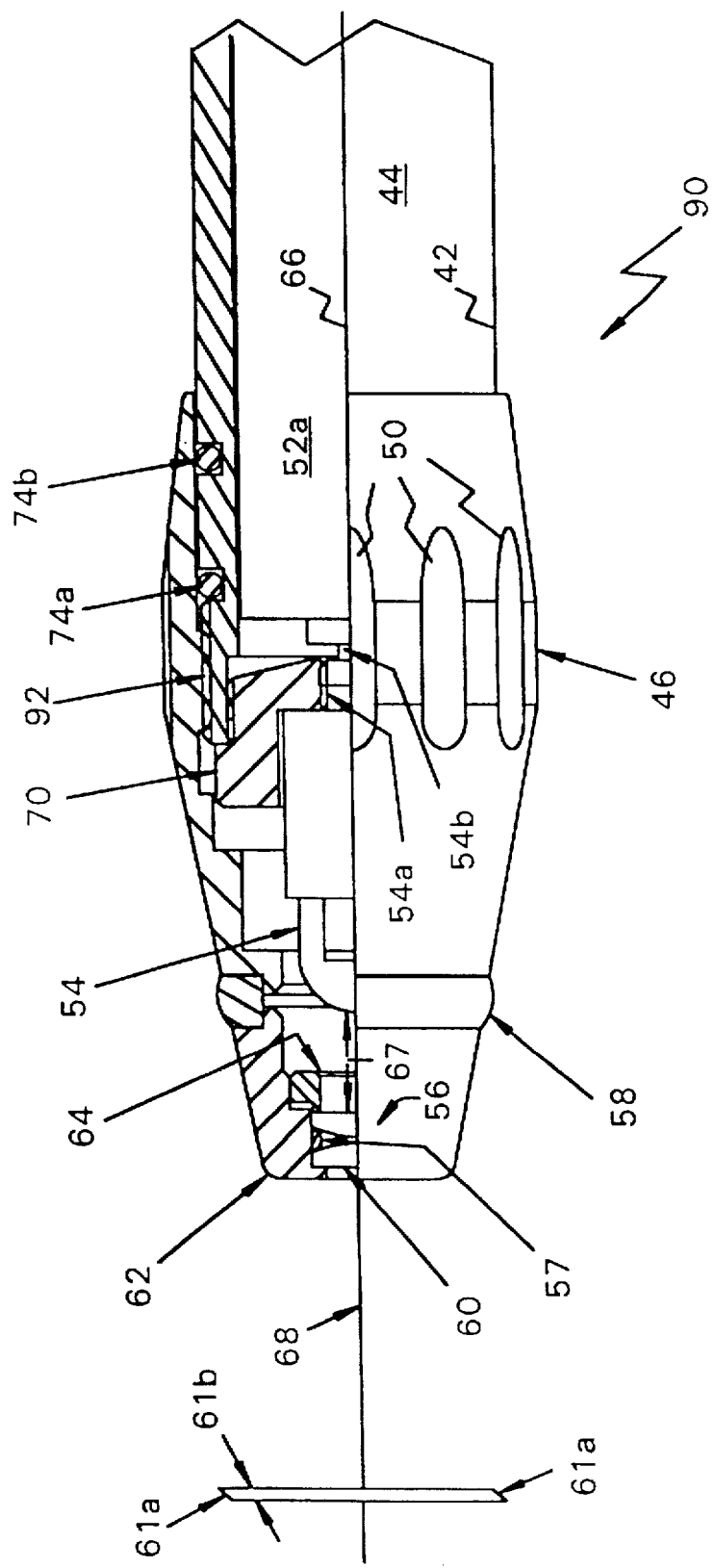
FIG. 2A illustrates additional detail of the front part of the instrument shown in FIG. 2, including the operation and interaction of the lamp and optics within the lamp body.

FIG. 2A shows additional detail of a front part 90, partially cut-away, of the instrument 40 of FIG. 2. As discussed above, the filament 54 is powered by an electrical circuit connected to battery 52a and actuated by the switch mechanism of knob 48. The retainer 70, in particular, abuts and holds the filament 54, and maintains, as part of the circuit, an electrical conduit between the filament electrode 54a and the handle 44.

The axial movement used to change the distance 67 between the filament 54 and the optics 56 changes the optical magnification of the slit image 61 (both length 61a and width 61b) and the working distance 68. The window 58 provides a visual indication of the instrument's current operating state, i.e., "ON" or "OFF," by permitting a user to comfortably view the light from the filament 54 through the knob 46.

A user of the instrument 40 changes the distance 67 selectively to adjust instrument magnification, typically by gripping the knob 46 on the grips 50 and rotating the knob 46 about the axis 66. This rotation is enabled by a threaded coupling 92 between the knob 46 and the handle 44. One suitable coupling 92, according to the invention, is known to those skilled in the art as a twenty pitch thread, or 20 t.p.i. (thread-per-inch). A 20 t.p.i. coupling 92 facilitates fine and smooth movement and control of the knob 46 relative to the handle 44. During this rotation, the optics 56 and/or the filament 54 rotate about the axis 66.

Other pitches may also be used within the coupling 92, for example, to modify the rate at which the rotation of the knob 46 changes the distance 67. Further, the threaded coupling 92 can incorporate (i) multi-start threading, such as the two-start, three-start or four-start threads known in the art, and/or (ii) left or right-handed threading, such as to change the direction of the axial movement for a given rotational twist.

The filament 54 and other components within the instrument 40 are protected, in part, by the O-rings 74a, 74b. The O-rings 74a, 74b are selected to be tight enough to seal out moisture, though not so tight as to induce unwanted rotational and/or translational friction between the knob 46 and handle 44.

The instrument 40 of FIG. 2 preferably utilizes a line filament lamp that are known in the prior art. By way of example, Propper Manufacturing, Inc., manufactures two suitable line filament lamps, identified by model numbers 199020 or 199028, that can be used in connection with the invention of FIGS. 2, 2A. Other suitable filament lamps are made, for example, by Reichert, Neitz.

Figure 2B:
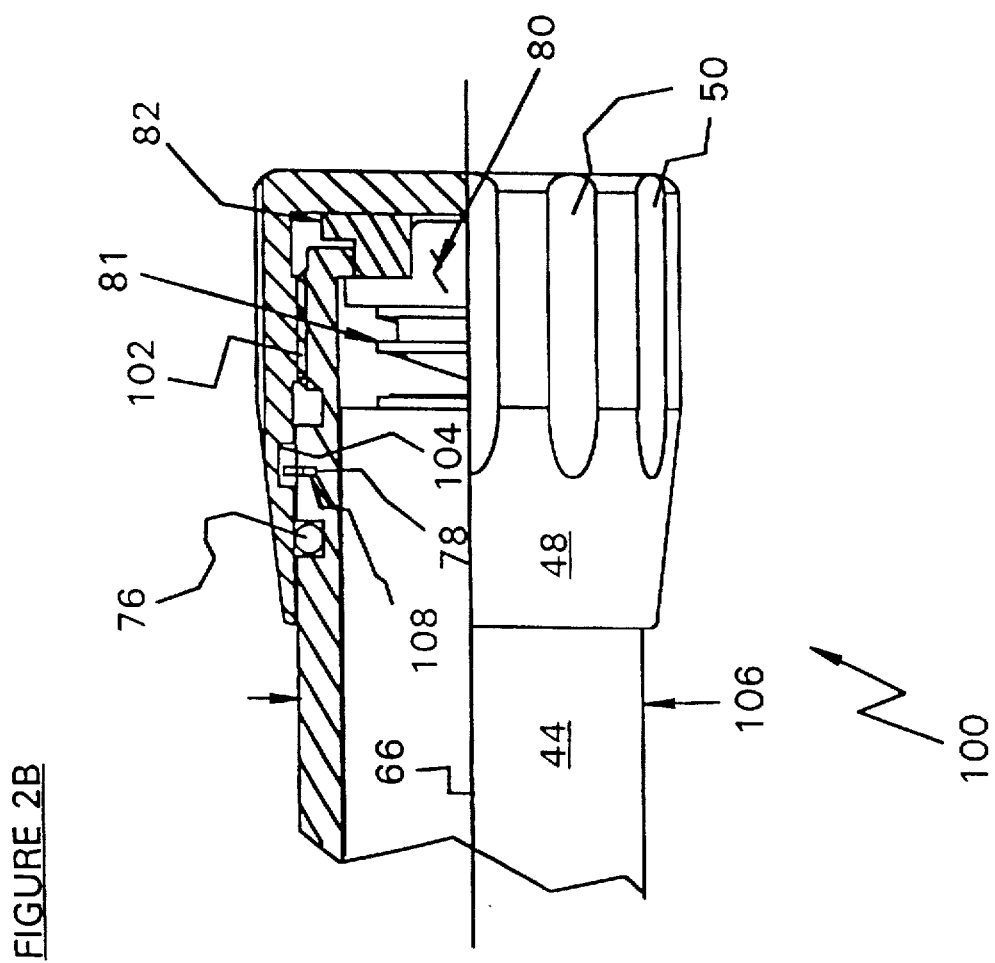
FIG. 2B illustrates additional detail of the rear part of the instrument shown in FIG. 2, including the operation of the switch mechanism which turns the instrument ON and OFF.

FIG. 2B shows additional detail of a rear part 100, partially cut-away, of the instrument 40 of FIG. 2. The knob 48 is, preferably, permanently connected over the handle 44 by way of the retaining ring 78, such as a Smalley Ring VS-75. The O-ring 76 seals the battery 52b, conductor spring 81, mount 80, and other internal parts against moisture and particulate matter; and further provides a source of friction to facilitate the smooth operation of the threaded coupling 92. The plastic insulator 82 functions integrally with the operation of the knob 48 to connect and disable the instrument circuitry, such as described in connection with FIG. 2C–2E.

As above, a user of the instrument 40 rotates the knob 48 selectively to turn the instrument "ON" and "OFF," typically by gripping the knob 48 on the grips 50 and rotating the knob 48 about the axis 66. This rotation is enabled by the threaded coupling 102 between the knob 48 and the handle 44. Like the coupling 92 of the knob 46, the coupling 102 preferably incorporates a 20 t.p.i. thread to provide fine and smooth rotational movement of the knob 48 relative to the handle 44.

Figure 2C:
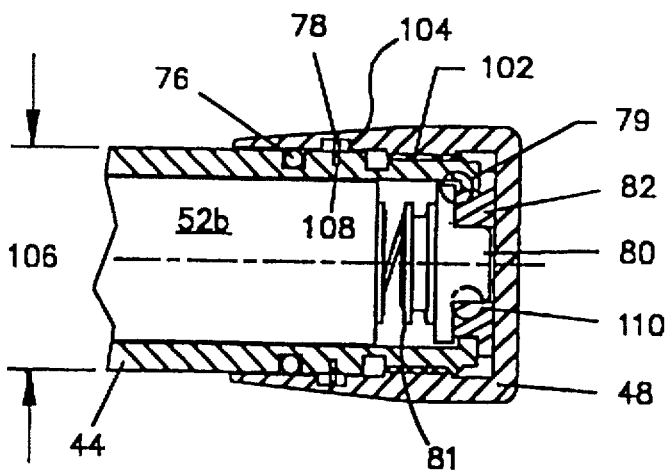
FIGS. 2C–2E illustrate, collectively, the operation of the switch mechanism enabled in the rear knob of the instrument of FIG. 2.

With reference to FIG. 2C, the knob 48 is fully rotated clockwise along threaded coupling 102 so that the instrument 40 is in the "OFF" position. In the "OFF" position, the electrical contact 79 is "OPEN" so that no electrical current is drawn through the battery circuit. Accordingly, the filament 54 of FIG. 2A is off and not generally visible through the window 58.

Figure 2D:
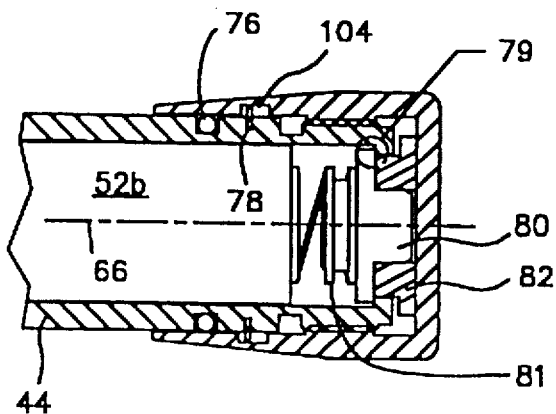

FIG. 2D, on the other hand, shows the instrument 40 in the "ON" position. In FIG. 2D, the knob 48 is rotated such that the electrical contact 79 is "CLOSED" and current is drawn through the circuit to power the line filament 54, FIGS. 2, 2A. With 20 t.p.i. threading for the coupling 102, this "ON" position occurs in a counter-clockwise rotation of 0.42 turns, i.e., nearly 180 degrees of revolution, relative to the "OFF" position of FIG. 2C.

Those skilled in the art will appreciate that the switch shown in FIGS. 2C–2D can be constructed to operate with differing degrees of revolution and/or direction, relative to the "ON" and "OFF" positions described above, without departing from the scope of the invention. For example, the thread pitch 102 can be altered to increase or decrease the axial travel per revolution. Further, the thread coupling 102 can incorporate multi-start threading, and either of left or right-handed threading. In a preferred embodiment of the invention, the coupling 102 incorporates 20 t.p.i. pitch and three-start threading, which facilitates the quick and smooth operation of the switch of FIGS. 2C and 2D.

The circuit which energizes the filament 54 through its electrodes 54a, 54b, FIGS. 2, 2A, is provided through several components of the instrument 40, including: the batteries 52a, 52b; the electrically conductive handle 44; the retaining element 70; the mount 80; and the conductive spring 81. In accord with the invention, when the knob 48 is rotated to the "ON" position, the mount 80 bridges the contact to the inner and conductive wall 99 of the handle 44, FIG. 2F below, so as to complete the circuit to the filament 54. By way of example, the handle 44 can be constructed of aluminum to form the circuit's conductive path between the retainer element 70 and the mount 80.

Figure 2E:
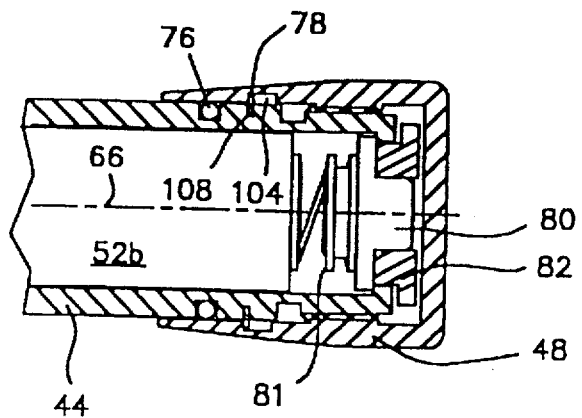

FIG. 2E illustrates a knob 48 that is fully rotated in a counter-clockwise direction of 0.42 turns beyond the switch position rotated to and described in connection with FIG. 2D. In this position, the instrument 40 stays "ON" and the inner groove 104 of knob 48 abuts the retainer 78 to form a stop against any further counter-clockwise rotation and travel in that direction.

Figure 2F:
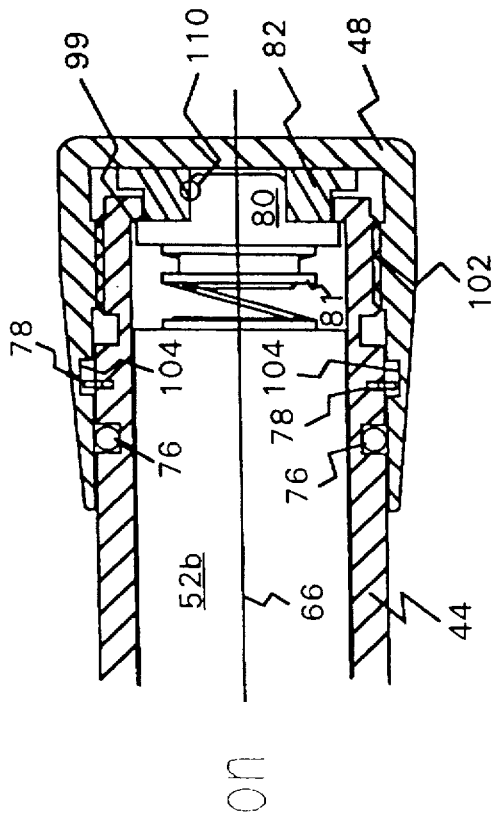
FIGS. 2F and 2G illustrate additional and enlarged detail of the ON and OFF mechanism of FIG. 2.
Figure 2G:
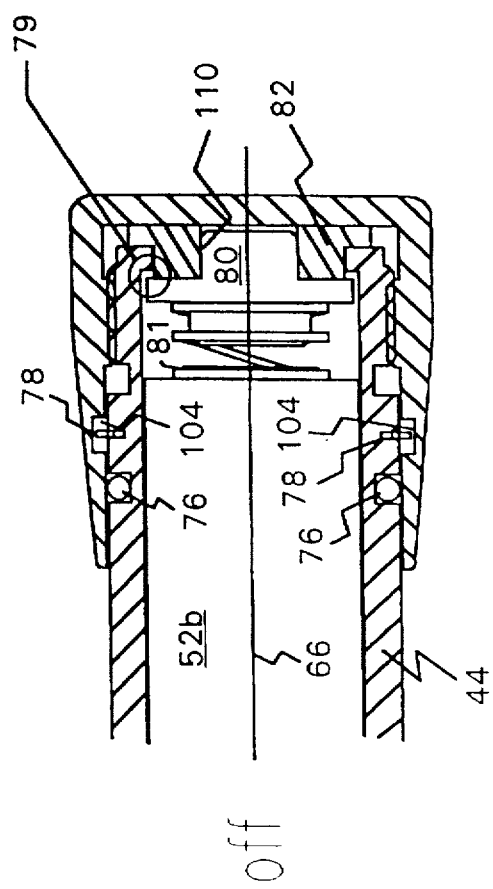
Figure 3:
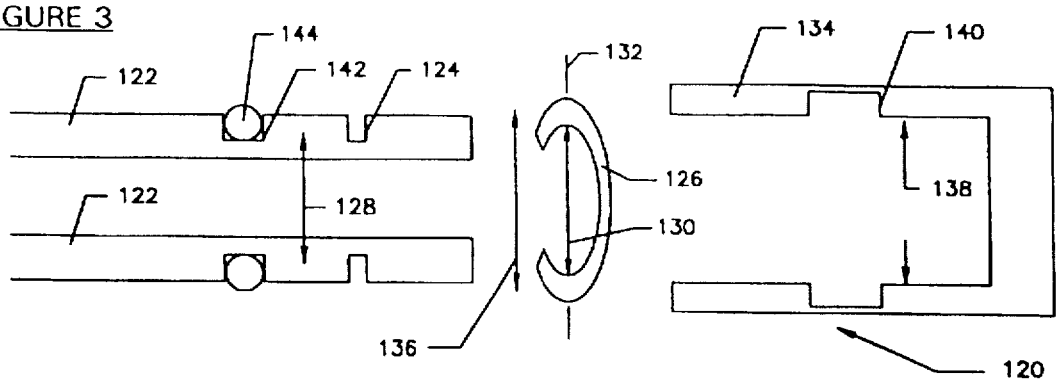
FIGS. 3–3A show a connector element constructed according to the invention and which is suitable for incorporating into the switch mechanism shown in FIGS. 2–2E.

Preferably, the groove 104 of FIGS. 2B–2E is formed integrally with the knob 48 so as to fit over the ring 78 during manufacture. More particularly, if, for example, the ring 78 is a Smalley Ring, known to those skilled in the art, the ring is C-shaped and can be compressed so as to fit within the inner diameter 106 of the knob 48. A retaining groove 108 seats the ring 78 and has an outer diameter which is less than the inner diameter of the ring 78, so that once the ring 78 is fitted within the groove 108, it can be compressed so that the knob 48 can slide or thread over the ring 78 and onto the handle 44. More particularly, by compressing the ring 78 within the groove 108, the knob 48 can be screwed onto the handle 44. Once the groove 104 of the knob 48 axially aligns with the groove 108, the ring 78 expands to within the groove 104, thereafter operating as a two-directional axial stop to prevent axial excursion of the knob 48 along the axis 66. FIGS. 2F and 2G illustrate the grooves 104, 108 in more detail; while FIG. 3 illustrates the manufacturing conveniences associated with the illustrated switch.

The O-ring 76 of FIGS. 2, 2B–2E is positioned and directed away from the groove 104 and contact 79 so as to seal out moisture and particulates.

The plastic insulator 82 of FIGS. 2, 2B–2E preferably forms a press fit 110 with the mount 80. By constructing the insulator 82 with relatively soft plastic and with an inner diameter that is about 0.001" smaller than the outer diameter of the mount 80, a suitable press fit 110 is achieved.

Preferably, the conductive springs 81 of FIGS. 2, 2B–2G engage the mount 80 in a "spring fit," known to those skilled in the art, so as to provide a sturdy and solid electrical coupling between the battery 52b and the mount 80.

FIGS. 2F–2G illustrate additional and close-up section views of the switch functionality provided by the knob 48 of FIG. 2. In particular, FIG. 2F shows the knob 48 in a rotated position which corresponds to when the instrument 40, FIG. 2, is "ON." FIG. 2G, by comparison, shows the knob 48 in a rotated position that corresponds to the instrument 40 being "OFF."

Figure 3A:
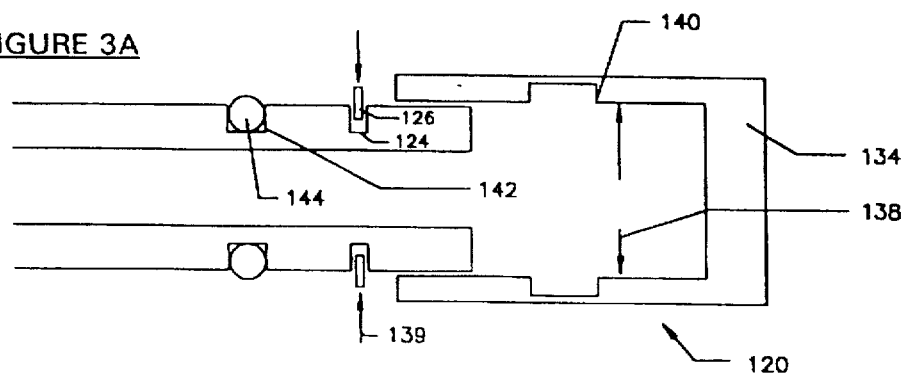
Figure 3B:
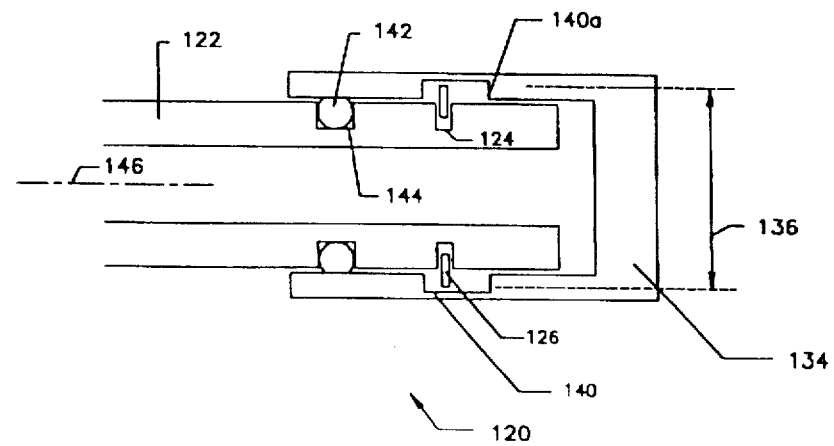

FIGS. 3, 3A and 3B illustrate the manufacturing benefits associated with the utilization of a Smalley Ring within a sealable switch, such as described above. FIG. 3 shows an exploded view of a three-piece connector 120 constructed according to the invention. As above, an inner body 122 has a groove 124 used to seat the Smalley ring 126 during integration. The inner diameter 128 of the groove 124 is smaller than the inner diameter 130 of the ring 126 so that the ring 126 can be seated within the groove 124 and compressed, along axis 132, to permit passage of the outer knob 134 over the outer diameter 136 of the ring 126.

FIG. 3A shows a first step in the integration of the ring 126 onto the inner body 122. Once the ring 126 is seated within the groove 124, the knob 134 slides over the inner body 122 (or, alternatively, the knob 134 is threaded over the body 122, such as the knob 48 of FIG. 2) until it reaches the ring 126, as illustrated. At this point, the ring 126 must be compressed, such as shown by arrows 139, so as to temporarily reduce the diameter 136 of the ring 126 so that the knob 134 can pass over the ring 126. Once the groove 140 of the knob 134 reaches the ring 126, the ring 126 expands to its natural diameter size 136, thereby inter-locking both grooves 124, 140 together, such as shown in FIG. 3B.

In the event that a moisture or other seal is desirable to prevent certain contaminations within the inner body 122 and knob 134, a second groove 142 within the inner body 122 provides a seating for an O-ring 144. The O-ring 144 seals against the inner diameter 138 of the knob 134, thus sealing the internal parts of the coupler 120 against contamination, e.g., water and/or particulate matter such as dust.

The axial travel of knob 134, along axis 146 of FIG. 3B and relative to the inner body 122, is restricted to the groove width 140a of the knob 134. A larger groove width 140a permits greater axial travel, while a narrower groove width 140a permits very limited axial travel.

The advantages of the coupler 120 shown in FIGS. 3–3B are several. For example, screws or other attachment devices are not needed between the inner body 122 and the knob 138. Accordingly, the manufacturing process is simplified, reducing costs. Further, the coupler 120 is tamper-resistant. That is, provided the coupler 120 is made of sturdy materials like aluminum, a rigorous and destructive process is required to undo the coupling between the inner body 122 and the knob 134. Such a coupling 120 is therefore useful in connection with children's devices and other systems which benefit by stream-lined manufacturing and tamper-proof couplers.

Figure 4:
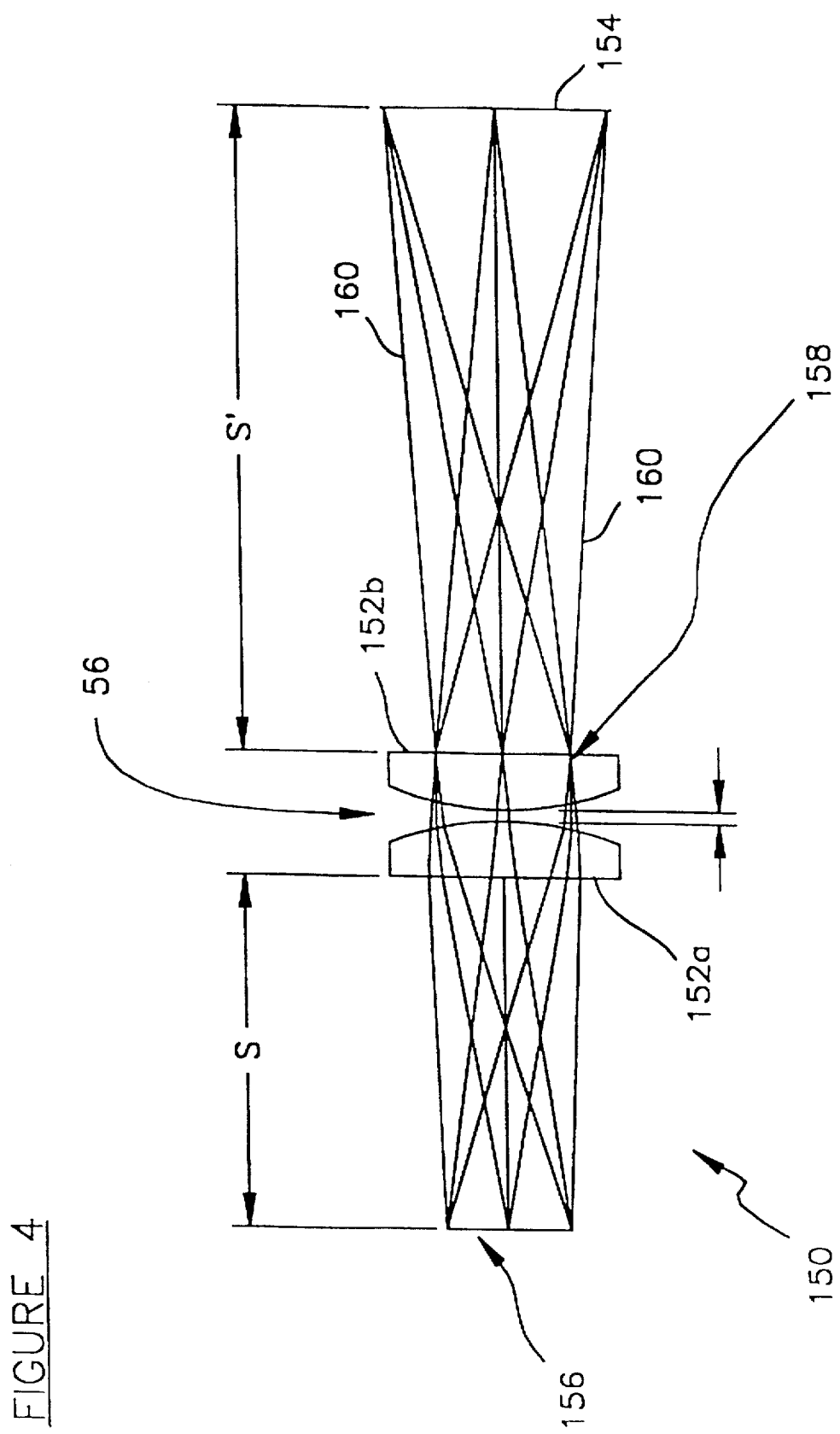
FIG. 4 illustrates one suitable optical prescription, constructed according to the invention, for use as the optical elements illustrated in connection with FIGS. 2 and 2A.

FIG. 4 illustrates one suitable optical layout 150 in accord with the invention and which includes a pair of optical elements such as the optical elements 56 of FIGS. 2 and 2A. Specifically, a pair of BaK2 plano-convex lenses 152a, 152b form an image 154 of the line filament object 156. Each of the lenses 152a, 152b has a radial curvature of 7.49 mm, a center thickness of 1.50 mm, and an outer diameter of 5.99 mm. The lenses 152a, 152b are separated by about 4.00 mm to provide an overall effective focal length of 7.01 mm. A stop 158 limits the extent of the axial rays 160 and the effective f-number of the resulting layout 150.

The lenses 152a, 152b magnify the line filament 156 according to the selected distance "S," which is similar to the distance 67 of FIG. 2A. By way of example, if "S" is set to 9.5 mm, the image distance, i.e., "S'," becomes 17.26 mm and the resulting system magnification is (17.26)/(9.5). Other magnifications are possible, in accord with the invention, by rotating the knob 46, FIG. 2, to thereby change the distance "S."

Accordingly, a hand-held slit lamp instrument which utilizes the optical layout 150 of FIG. 4 can adjust the magnification to select either the image width and length, or the working distance "S'" between the optics 152a, 152b and the resulting image 154.

Figure 4A:
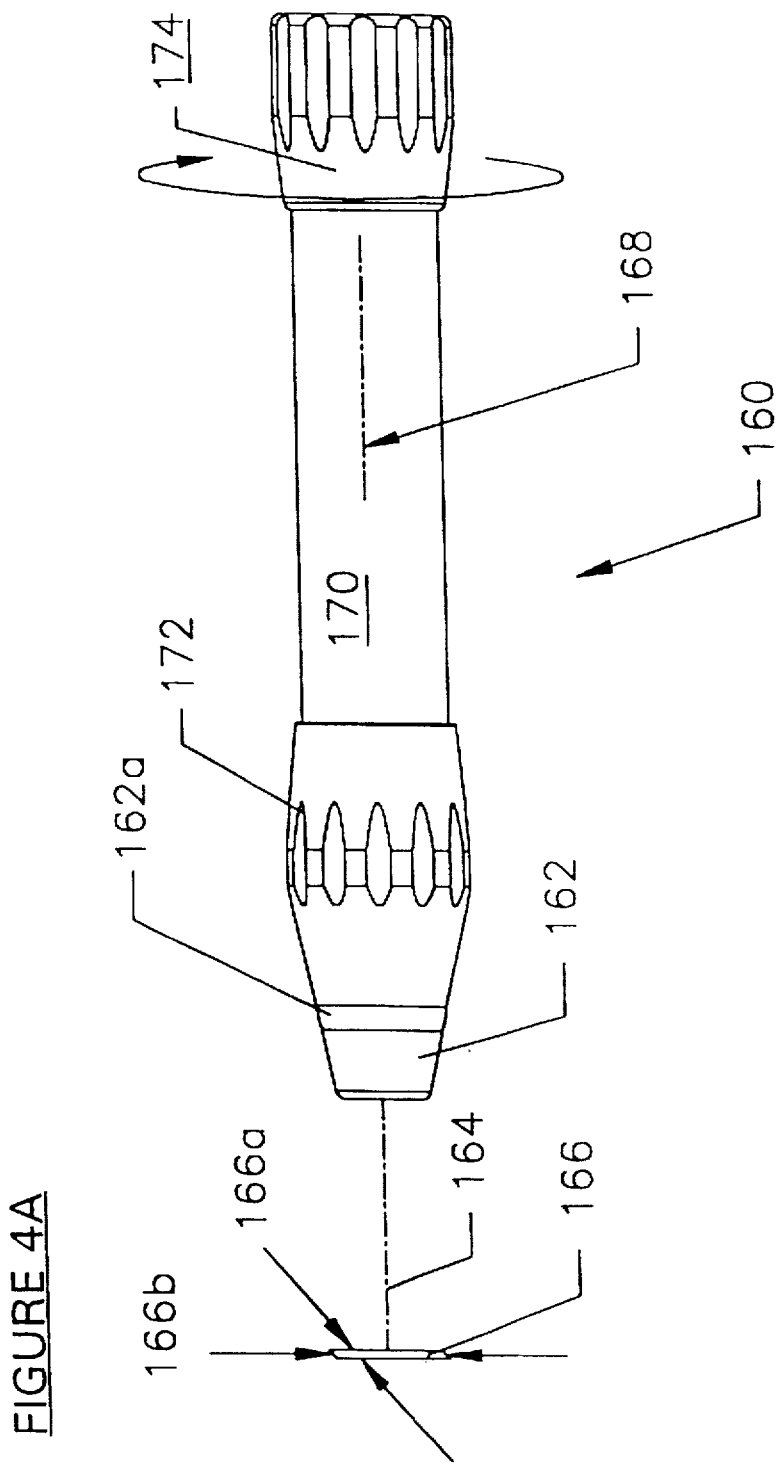
FIG. 4A illustrates an alternative hand-held slit lamp constructed according to the invention, and which provides for variable slit width magnification and selectable working distance.

Another suitable slit lamp, according to the invention, is shown in FIG. 4A. In particular, FIG. 4A shows an instrument 160 that includes a zoom lens 162, such as known to those skilled in the art, to vary either of (i) the working distance 164 between the instrument 160 and the resulting slit image 166, or (ii) the magnification of the slit image 166. A zoom ring 162a provides for optical adjustment of the zoom lens 160; while, as above, the rotation of the lens 162 about the axis 168, such as by rotating the lens 162 relative to the handle 170 via the grips 172, facilitates the adjustment of one other of (i) the working distance 164 between the instrument 160 and the resulting slit image 166, and (ii) the magnification of the slit image 166. In this way, the user of the lamp 160 can select both the working distance 164 and the size of the slit image 166 independently.

There are several advantages of the invention. First, the hand-held slit lamp instrument described herein is ergonomic and provides a bright, controllable and high contrast image to facilitate use within various settings, such as within the office, classroom, ambulance, intensive care unit, emergency room, and pediatric, veterinary and geriatric clinics. In accord with the invention, the hand-held slit lamp can also be sterilized, without degradation and as described herein, and can thus be used in an operating room environment.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed as new and secured by Letters Patent is:

1. A tamper-proof electrical switch, comprising:

an elongated inner body having a first outer diameter and relay means for connecting the inner body to a power source, the inner body having a first outer groove with a second outer diameter that is less than the first outer diameter;

a C-ring mounted with the outer groove and having (i) a first inner diameter that is greater than the second outer diameter and less than the first outer diameter, and (ii) a third outer diameter that is greater than the first outer diameter, the C-ring being flexible to sustain temporary compression of the first inner diameter;

an elongated outer body rotatably threaded with the inner body, the outer body being rotatable relative to the inner body for controlling axial displacement of the outer body relative to the inner body, the outer body having a second inner diameter that is greater than the first outer diameter and less than the third outer diameter, and an inner groove with an inner diameter that is greater than the third outer diameter, the inner groove and the outer groove being substantially concentric wherein the C-ring forms a stop against the inner groove and between a first position and a second position; and connect means, responsive to the axial displacement of the outer body, for engaging the relay means at the first position to complete a circuit with the power source, and for disengaging the relay means at the second position to break the circuit.

2. A switch according to claim 1, wherein the C-ring comprises a Smalley ring.

3. A method of forming an electrical switch, comprising the steps of:

fitting a C-ring over an elongated inner body, the inner body having a first outer diameter and a first outer groove with a second outer diameter that is less than the first outer diameter, the C-ring having (i) a first inner diameter that is greater than the second outer diameter and less than the first outer diameter, and (ii) a third outer diameter that is greater than the first outer diameter;

compressing the C-ring and threading an elongated outer body with the inner body and over the C-ring by rotating the outer body about the elongated axis of the inner body, the outer body having a second inner diameter that is greater than the first outer diameter and less than the third outer diameter, and an inner groove with an inner diameter that is greater than the third outer diameter; the step of threading including the step of aligning the inner and outer grooves such that the C-ring expands to within the inner groove; and rotating the outer body to control an axial displacement of the outer body, relative to the inner body, between a first position that completes an electrical circuit, and a second position that breaks the electrical circuit.

* * * * *